United States Patent [19]

Albert

[11] Patent Number: 4,730,350
[45] Date of Patent: Mar. 8, 1988

[54] METHOD AND APPARATUS FOR SCANNING X-RAY TOMOGRAPHY

[76] Inventor: Richard D. Albert, 317 Hartford Rd., Danville, Calif. 94526

[21] Appl. No.: 854,083

[22] Filed: Apr. 21, 1986

[51] Int. Cl.⁴ ............................................. G01N 23/08
[52] U.S. Cl. ........................................ 378/10; 378/12; 378/99
[58] Field of Search ................. 378/10, 12, 22, 23, 378/99, 19, 62, 57

[56] References Cited

U.S. PATENT DOCUMENTS

| | | | |
|---|---|---|---|
| 3,499,146 | 3/1970 | Richards | 378/23 |
| 3,778,614 | 12/1973 | Hounsfield | 250/362 |
| 3,949,229 | 4/1976 | Albert | 250/401 |
| 4,002,917 | 1/1977 | Mayo | 250/445 |
| 4,144,457 | 3/1979 | Albert | 250/445 |
| 4,149,076 | 4/1979 | Albert | 250/402 |
| 4,196,351 | 4/1980 | Albert | 250/416 TV |
| 4,234,794 | 11/1986 | Voinea et al. | 378/12 |
| 4,288,697 | 9/1981 | Albert | 250/505 |

*Primary Examiner*—Janice A. Howell
*Assistant Examiner*—David P. Porta
*Attorney, Agent, or Firm*—Donald J. McRae

[57] ABSTRACT

Tomographic or sectional X-ray images (46) of a subject (32) are obtained rapidly by a method and apparatus that do not inherently require motion of the X-ray source (12) and detectors (13) or motion of the subject in order to generate the tomographic image data. In the source, a charged particle beam (17) is directed to a broad target plate (18) and raster scanned to produce a moving X-ray origin point (19). X-ray count values are obtained at a plurality of spaced apart detection points (D1, D2, D3, D4, D5, D6, D7) situated at the opposite side of the subject from the source. Successive count values from a first detection point are combined with successive count values from at least one other detection point that originated at a later time in the course of the raster scan to provide a sequence of composite data values. Display of an image of at least a portion of the raster scan which exhibits variations between successive values of the composite data provides an image in which data from a specific plane (31a, 31b) within the subject is emphasized while data from other planes is suppressed. The apparatus may be compact and inexpensive in comparsion with tomographic installations that are dependent on precisely controlled motion of components or the subject during scanning.

27 Claims, 13 Drawing Figures

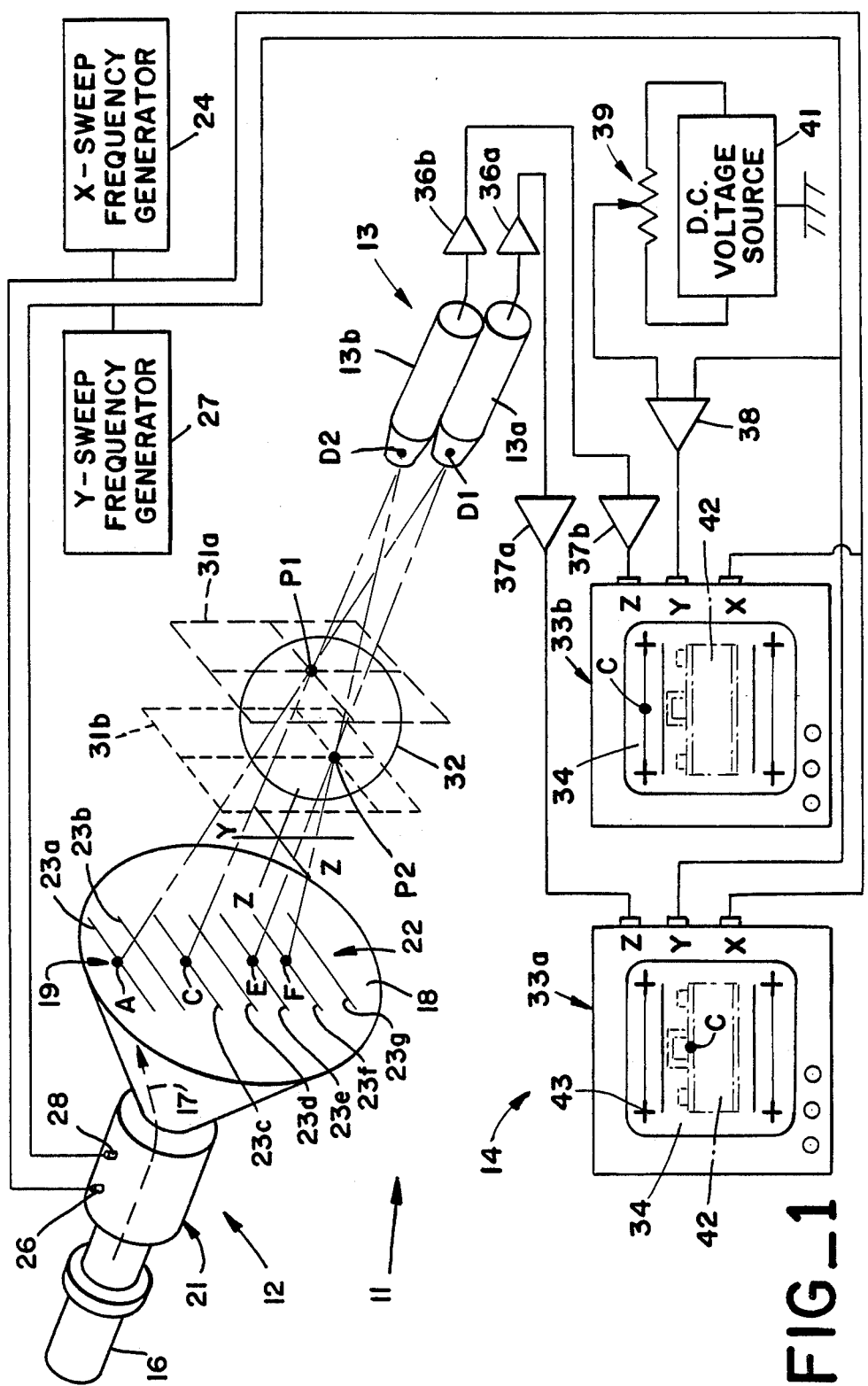
FIG_1

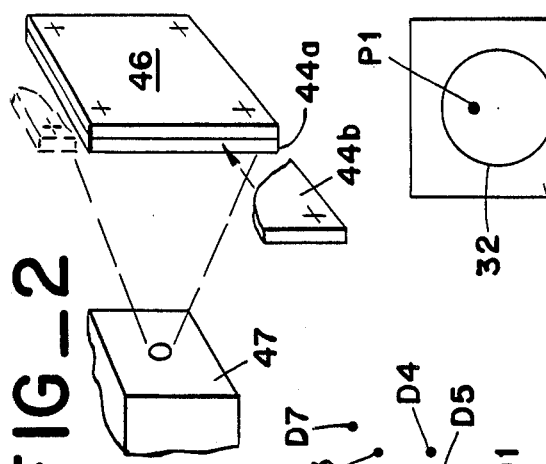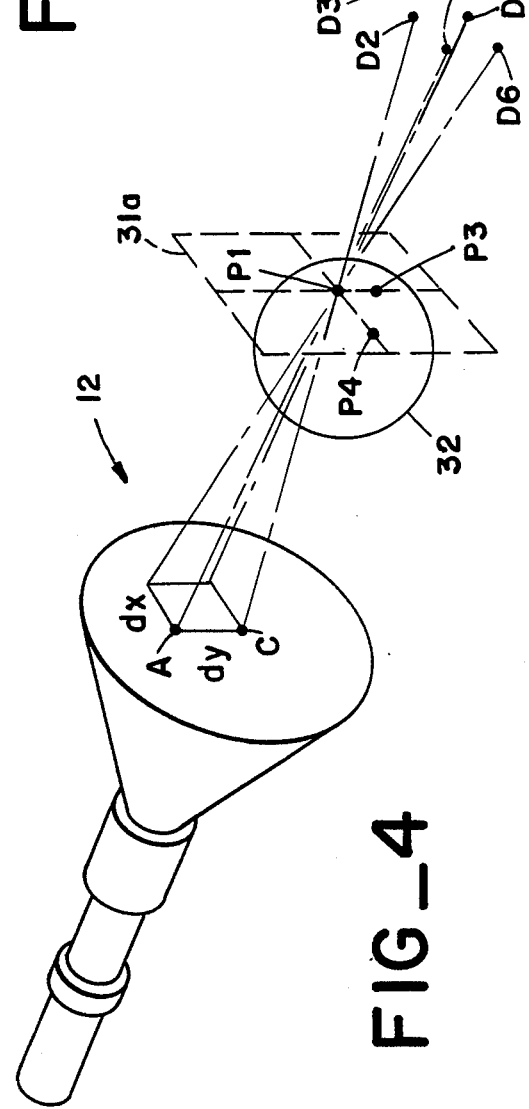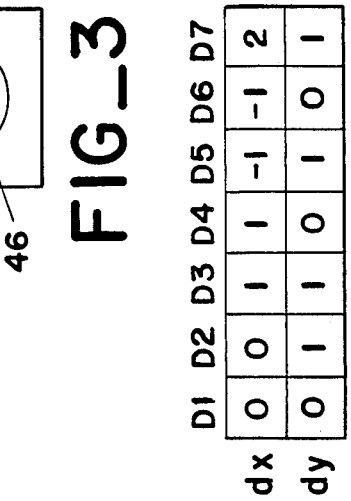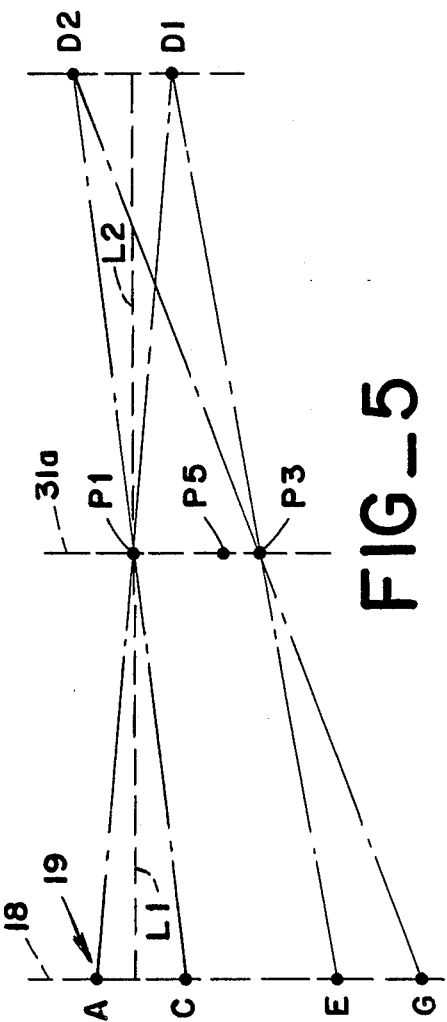
FIG_2
FIG_3
FIG_4
FIG_5
| | D1 | D2 | D3 | D4 | D5 | D6 | D7 |
|---|---|---|---|---|---|---|---|
| dx | 0 | 0 | 1 | 1 | -1 | -1 | 2 |
| dy | 0 | 1 | 1 | 0 | 1 | 0 | 1 |
FIG_6

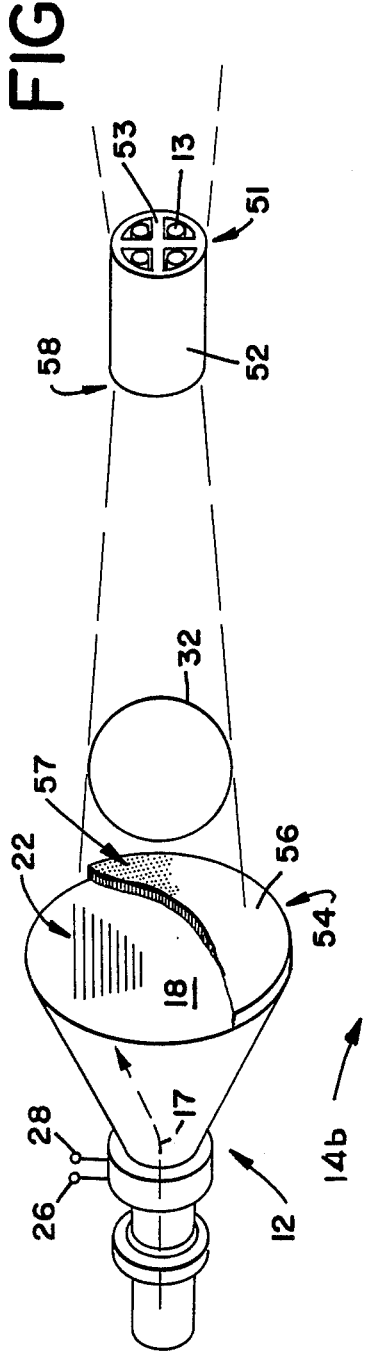
FIG_7
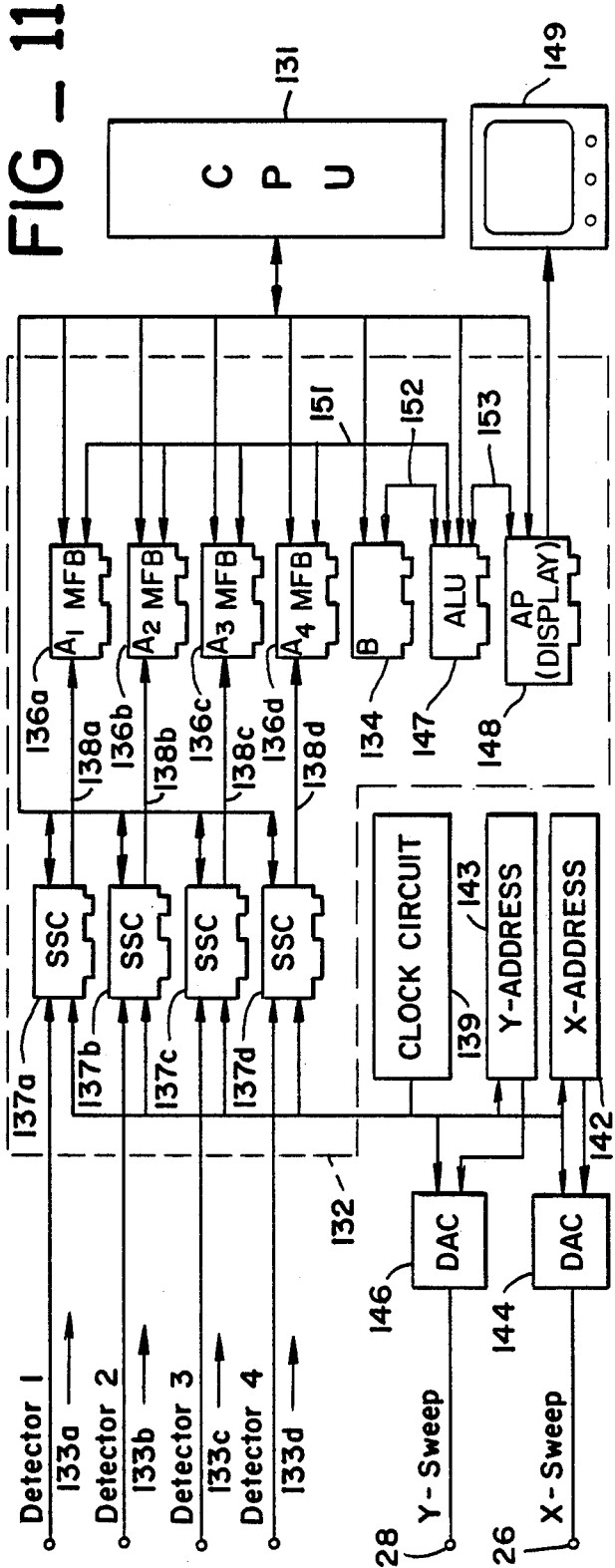
FIG_11

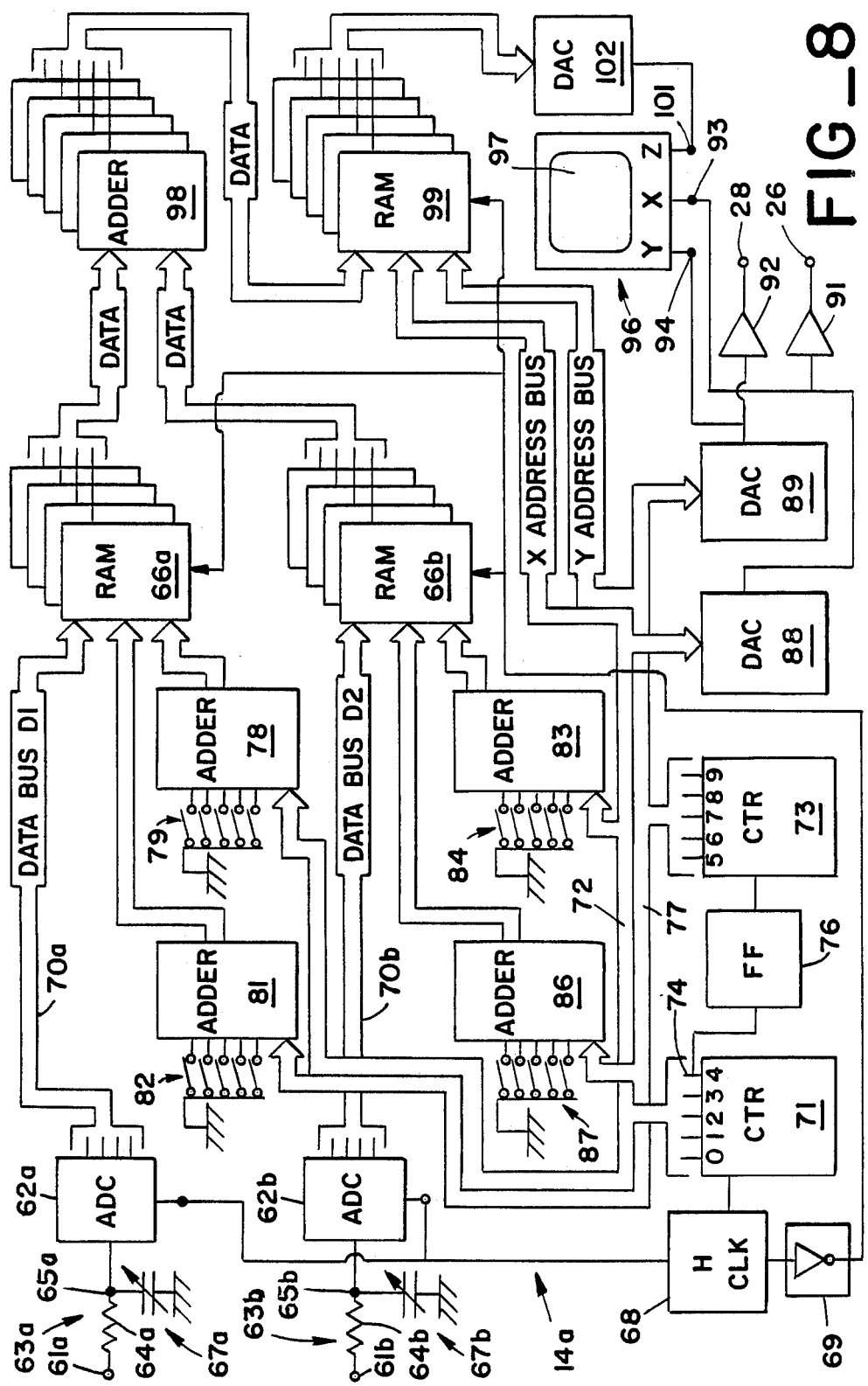

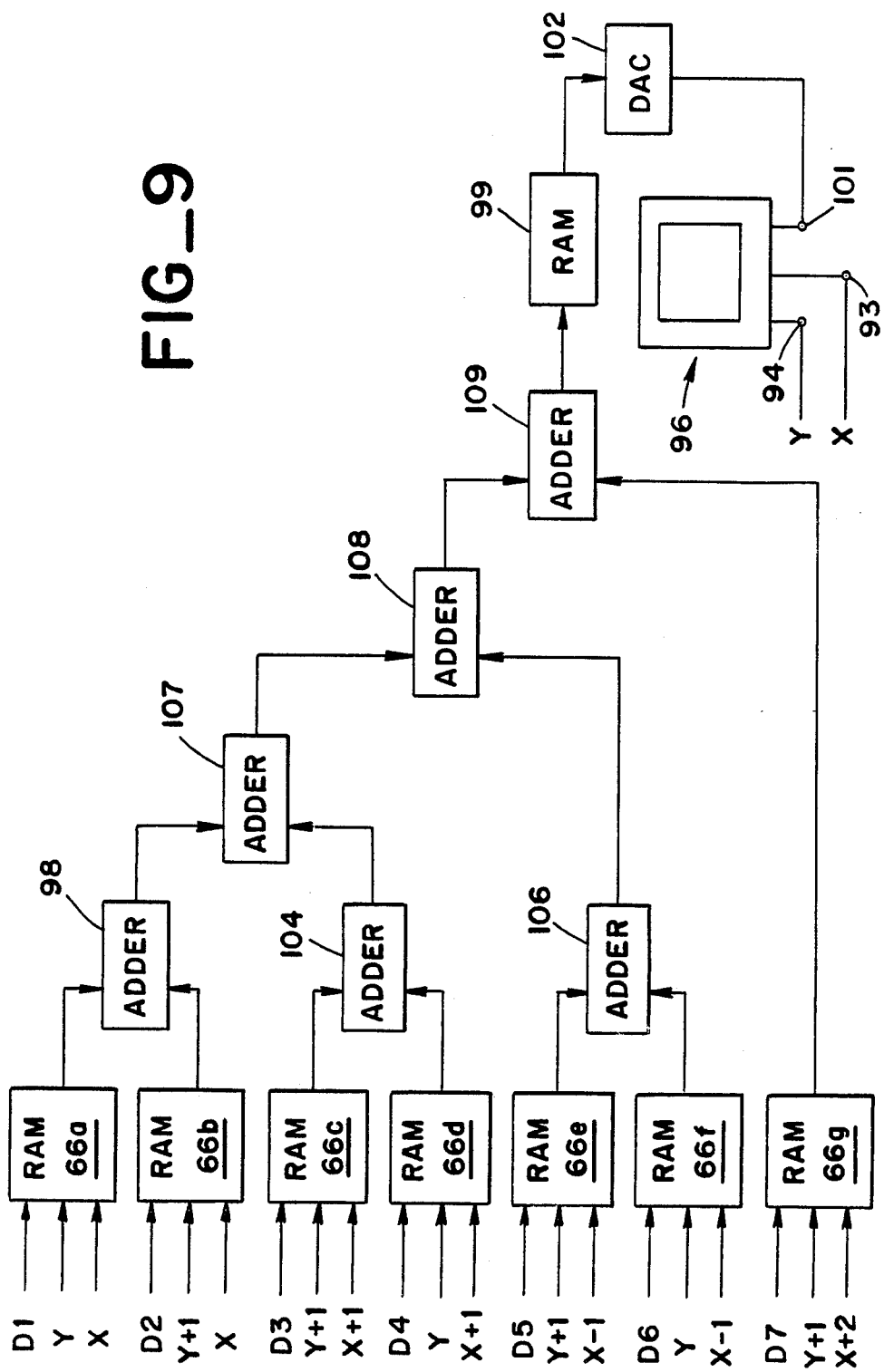
FIG_9

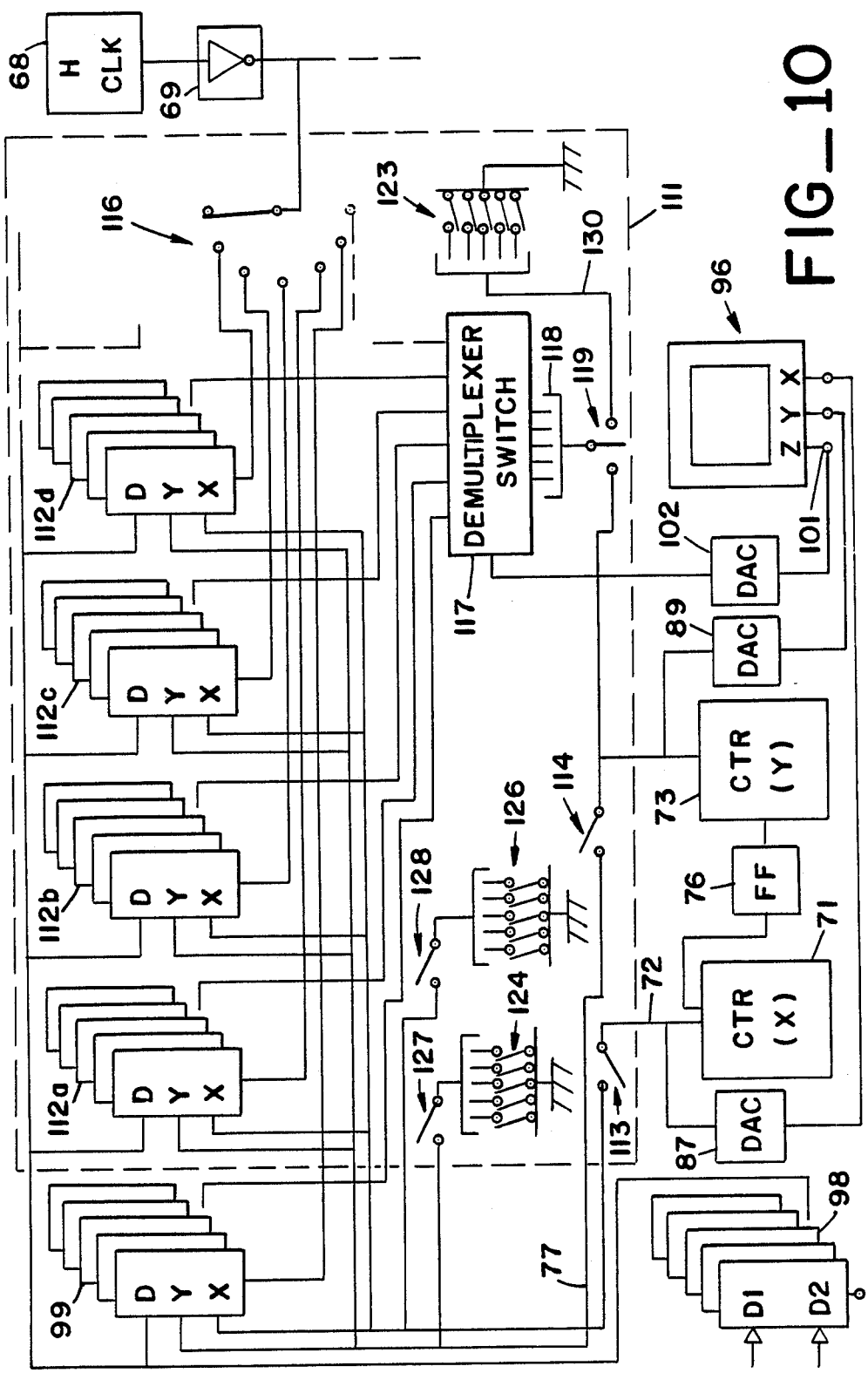

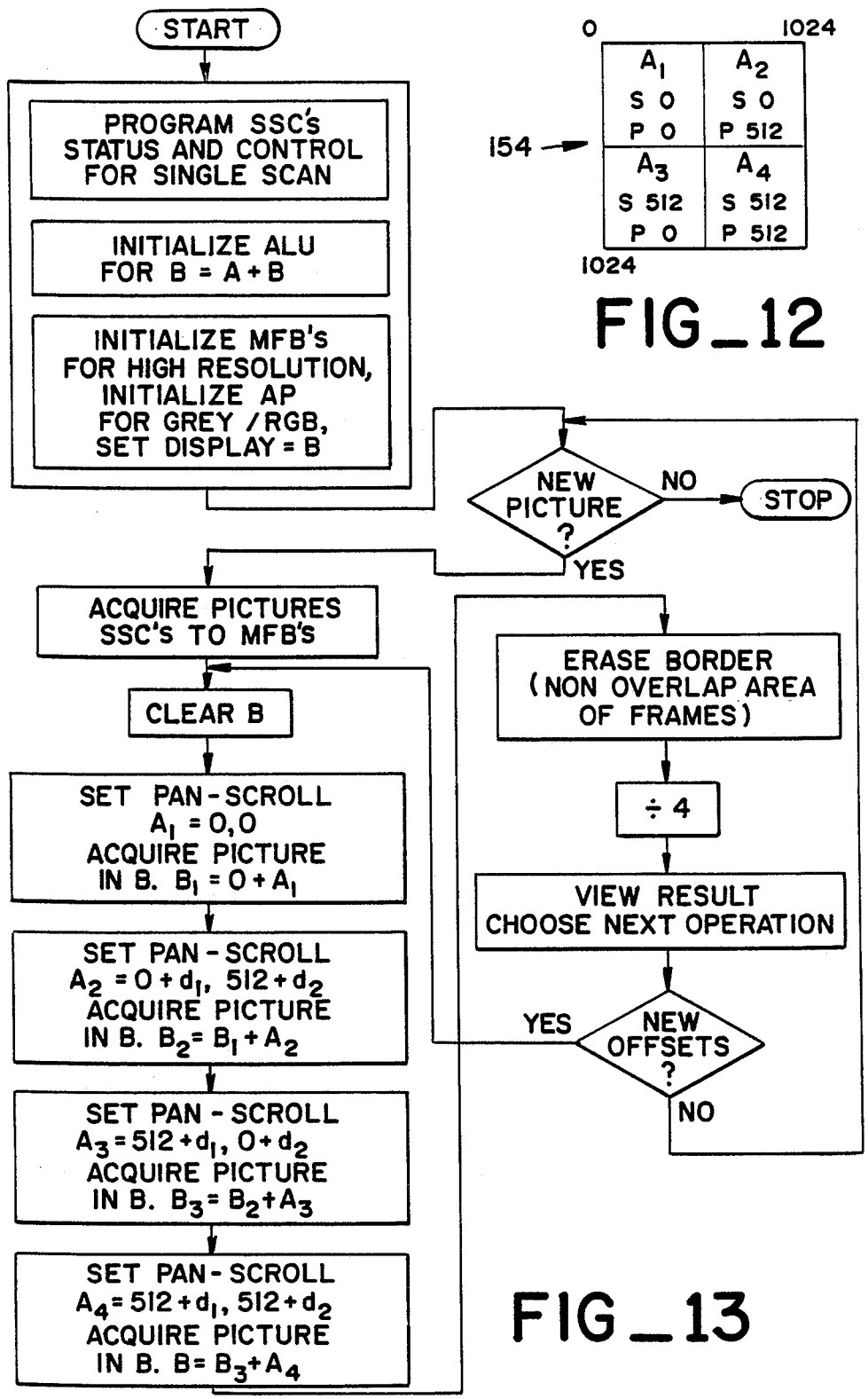

METHOD AND APPARATUS FOR SCANNING X-RAY TOMOGRAPHY

TECHNICAL FIELD

This invention relates to the production of X-ray images and more particularly to tomographic methods and apparatus for generating sectional radiographic images of the interior of a subject.

BACKGROUND OF THE INVENTION

X-ray images produced by non-tomographic techniques are often difficult to interpret and may fail to provide needed information about a medical patient or an inanimate object that is being examined for structural flaws. Data originating from a specific internal region of particular interest may be obscured by overlapping or superimposed imaging of other regions that are forward from or behind the region of interest.

The more recently developed tomographic X-ray imaging techniques are not subject to the above discussed disadvantage. Computer aided tomography can generate a cross sectional depiction of a single plane that is essentially free of data arising from other planes within the subject. Variations of X-ray absorbency between different areas of the imaged plane are made apparent without ambiguity as to location and with much greater clarity than is usually realizable with older techniques.

Most prior tomographic X-ray installations require a bulky, elaborate and costly mechanical scanning system. Installations of this kind have an X-ray source which directs a narrow X-ray beam to a detector at the opposite side of the subject. The source and detector are jointly translated relative to the subject, or the subject itself may be translated, so that the X-ray beam cuts across a plane within the subject that is to be imaged. A single translation of this kind cannot provide a meaningful tomographic or sectional image. The location of points within the plane where a change of X-ray absorbency was detected can be determined with respect to one coordinate but not with respect to the orthogonal coordinate. Consequently it is necessary to turn the source and detector angularly relative to the subject and repeat the translation. The location of the points in both coordinates than becomes determinable by data processing operations comparable to triangulation.

As a practical matter it is usually necessary, in such installations, to perform a large number of translations of the source and detector alternated with a large number of angular repositionings of such components in order to generate an image of desirable resolution and clarity. The mechanisms which enable the source and detector or the subject to be traveled through this repetive combination of linear and angular motions accounts for a considerable part of the bulk, complexity and cost of such installations. The mechanical positioning and scanning structure becomes even more complex if sectional images of more than one plane or of oblique planes are to be generated from a single scanning sequence.

Disadvantages of scanning X-ray installations of the above discussed kind are not limited to size, complexity and cost. An undesirably long period of time is required to perform the mechanical scanning operations. This limits productivity and prolongs the radiation exposure of the subject. The effects of scattered X-rays decrease resolution in a tomographic image and long exposure times aggravate such image degradation.

The problems discussed above are alleviated to a considerable extent by another form of tomographic X-ray scanning system described in my prior U.S. Pat. No. 4,144,457. In the method and apparatus described in that prior patent, the X-ray source has an electron beam which is electrostatically or magnetically deflected to establish a moving X-ray origin point at a broad target plate. Thus the translation portion of the scanning operation is accomplished electronically without necessarily requiring physical movement of the source and detector or the subject for those portions of the scanning operation. Angular motion of the source and detector or the subject continues to be necessary between electronic translations but the mechanism for the purpose can be relatively compact and simple as only simple rotational motion is needed.

The apparatus of my above identified prior patent can be mechanically simpler, more compact and less costly than the wholly mechanical scanning systems which have been hereinbefore discussed. Electronic scanning can be conducted more rapidly than mechanical scanning thereby increasing productivity, decreasing radiation exposure of the subject and with a reduction of image degradation from scattered X-rays.

The above discussed advantages of electronic scanning would become even more pronounced if it were possible to generate a tomographic image without necessarily relying on any relative movement of the source and detector or the subject. Heretofore it has appeared that it is not possible to extract the data that is needed for generating a tomographic iamge in the absence of physical repositionings of the source and detector or subject during the course of scanning operations.

The present invention is directed to overcoming one or more of the problems discussed above.

SUMMARY OF THE INVENTION

In one aspect, the present invention provides a method of producing a tomographic image of a subject that includes the steps of generating X-rays at a moving origin point by directing a charged particle beam to a target surface, deflecting the charged particle beam to travel the origin point through a predetermined raster scan at the surface, detecting X-ray intensity during the course of the raster scan at a plurality of spaced apart detection points situated at the opposite side of the subject from the origin point, generating a first sequence of data values that is indicative of variations of X-ray intensity at a first detection point at successive times during the course of the raster scan and generating at least a second sequence of data values that is indicative of variations of X-ray intensity at a second detection point at successive times during the course of the same successive raster scan. Individual data values of the first sequence that are generated by X-rays from successive particular locations in the raster scan are combined with at least individual data values of the second sequence that are generated by X-rays from predetermined successive different locations in the same raster scan in order to produce a composite sequence of data values. An image corresponding to at least a portion of the raster scan is produced which depicts variations of the magnitude of successive data values of the composite sequence.

In another aspect, the invention provides tomographic imaging apparatus having an X-ray source in which a charged particle beam is directed to a target surface to generate X-rays at an origin point at the surface and which has beam deflection means for moving the origin point through a raster scan at the surface. The apparatus includes a pluraliuty of X-ray detectors which are spaced apart from the X-ray source and positioned to detect X-rays at separate detection points. The detectors include a first detector that transmits a first sequence of data values indicative of variations of X-ray intensity at a first of the detection points at successive times during the course of the raster scan and at least a second detector which transmits a second sequence of data values that is indicative of variations of X-ray intensity at a second of the detection points at successive times during the course of the same raster scan. The apparatus further includes means for combining individual data values from the first detector that are generated by X-rays from successive particular locations in the raster scan with at least individual data values of the second sequence that are generated by X-rays from predetermined successive different locations in the same raster scan in order to produce a composite sequence of data values. The apparatus still further includes means for displaying an image corresponding to at least a portion of the raster scan which depicts variations of the magnitude of successive data values of the composite sequence.

The invention does not inherently require motion of mechanical components of the X-ray source and detectors or movement of the subject itself in order to generate tomographic image data although some repositioning of components relative to the subject may be desirable for other reasons in some operations. Data needed for constructing a tomographic image can be obtained more rapidly than is possible with mechanical scanning systems which rely wholly or in part on actual movement of the X-ray source and detectors relative to the subject. Consequently, more scanning operations can be accomplished in a given time, radiation exposure of the subject may be reduced and less image degradation from scattered X-rays is present. The invention enables tomographic imaging of planes that are essentially perpendicular to the direction of X-ray travel through the subject and, in some embodiments, enables such imaging of planar or non-planar sections having other orientations. Radiology facilities embodying the invention may be compact and substantially less costly than older tomographic imaging installations in which scanning is accomplished in whole or in part by motion of heavy components.

BRIEF DESCRIPTION OF THE DRAWINGS

FIG. 1 depicts tomographic X-ray imaging apparatus in accordance with a first embodiment of the invention, certain components being shown in perspective and certain other components being shown in schematic circuit form.

FIG. 2 is a diagram illustrating steps which may be used to produce a tomographic image on film during the practice of some embodiments of the invention.

FIG. 3 is a view of a tomographic image on film as produced by the steps shown in FIG. 2.

FIG. 4 is a more diagrammatic view of certain components of the apparatus of FIG. 1 that facilitates understanding of the principles of operation.

FIG. 5 is a diagram of selected X-ray paths in the apparatus of the preceding figures which further facilitates understanding of the principles of operation.

FIG. 6 is a chart showing image offsets used in systems having a plurality of X-ray detectors.

FIG. 7 is a perspective view of additional elements which may be used to reduce radiation exposure of the of the subject and to reduce scattered X-ray effects.

FIG. 8 is a digital circuit diagram depicting one form of data processing system which may be used to generate tomographic images from the output of X-ray detectors that receive X-rays transmitted through a subject as shown in FIG. 1.

FIG. 9 is a digital circuit diagram illustrating additional components which may be combined with the circuit of FIG. 8 when a larger number of X-ray detectors are used in the scanning operations.

FIG. 10 is a digital circuit diagram illustrating still additional components which may be combined with the circuit of FIG. 8 to obtain tomographic images of planes or curved sections having different orientations than the images which are produced in the absence of the additional components.

FIG. 11 is a circuit diagram showing another digital data processing system for producing tomographic image data from the output of the X-ray detectors.

FIG. 12 is a diagram depicting data storage conditions in frame buffers of the system of FIG. 11.

FIG. 13 is a computer program flow chart applicable to the data processing system of FIG. 11.

DESCRIPTION OF THE PREFERRED EMBODIMENTS

Referring initially to FIG. 1 of the drawings, the primary components of tomographic imaging apparatus 11 in accordance with a first embodiment of the invention include an X-ray source 12 and a plurality of X-ray detectors 13 which perform the scanning operations and data processing means 14 for generating image data from the detector output signals.

X-ray source 12 may be of the known form, as described in my prior U.S. Pat. No. 3,949,229 for example, having an electron gun 16 which directs an electron beam 17 to a broad target plate 18 to establish an X-ray origin point 19 at the target plate. A deflection yoke 21, which may be of either the magnetic or electrostatic type, provides for deflection of electron beam 17 to sweep the X-ray origin point 19 through a raster scan 22 at target plate 18. Raster scan 22 in this example is of the rectilinear type in which the origin point 19 is traveled in the X coordinate direction along a series of spaced apart substantially parallel scan lines 23a to 23g although it is possible to use other raster scan patterns. To produce the raster scan 22, an X-sweep frequency generator 24 applies a repetitive ramp signal voltage to the X terminal 26 of yoke 21 while a Y-sweep frequency generator 27 applies a lower frequency ramp signal voltage to the Y terminal 28 of the yoke.

For clarity of illustration and to provide for an explanation of the principles of operation which will be hereinafter set forth, the raster scan 22 is shown in FIG. 1 and in subsequent figures with fewer scan lines 23 than are typically present and with greater scan line spacing than is normally the case. Raster scan parameters of the kind found in commercial cathode ray tube devices, such as oscilloscopes or television picture tubes are usually preferably but are not essential in all cases depending on the degree of resolution which is needed in the tomographic images. In general, resolution is increased by increasing the number of scan lines 23 per unit area of the target plate 18.

Two detectors 13a and 13b are used in this particular embodiment of the invention although it is advantageous to use a larger number in many cases as will hereinafter be discussed. The detectors 13 are of the scintillation and photomuliplier tube type in this example but may alternately be of any of the other known forms of X-ray detector that produce electrical output signal voltages in response to detection of X-rays at a small point-like X-ray sensitive region of the detector. The detection points D1 and D2 of detectors 13a and 13b respectively are spaced apart in a direction parallel to the plane of the raster scan 22, the detection points being spaced apart in the Y coordinate direction of the raster scan in this example although the spacing may also be in the X coordinate direction in some cases. Detection points D1 and D2 are equidistant from the plane of raster scan 22 and preferably equidistant from the center of the raster scan although compensating adjustments can be made in the data processing operations in circumstances where these preferred geometrical relationships are not met.

The output signals from detectors 13a and 13b may be a series of distinct voltage pulses each indicative of an individual X-ray in instances where the rate of detection of X-rays at points D1 and D2 is low. More commonly such output signals are continuous voltages which vary in magnitude as the rate of detection of X-rays at points D1 and D2 varies during the course of a scanning operation. In either case, the output voltages in effect provide sequences of data values indicative of variations of X-ray flux intensity which occur at detection points D1 and D2 during the course of a raster scan. Production of a tomographic or sectional image of a selected plane 31a within a subject 32 then includes the step of combining successive data values produced by one of the detectors 13 with successive data values that are produced by the other detector a predetermiend interval later during the course of the raster scan to produce a sequence of composite data values. An image corresponding to at least a portion of the raster scan 22 is then generated in which successive points along the raster scan exhibit variations corresponding to variations between successive data values of the composite sequence. Such an image is a tomographic depiction of the selected plane 31a as a result of effects which will be hereinafter described.

Data processing means 14 for performing the above described steps may take a variety of forms including both digital and analog systems. An analog system will be described initially as the principles of operation of the invention are more easily understood when considered in that context.

In particular, the data processing means 14 of FIG. 1 includes first and second display devices 33a and 33b, such as cathode ray tube oscilloscopes for example, of the type that generate visible images at screens 34 in response to horizontal or X-axis sweep frequency signals, vertical or Y-axis sweep frequency signals and Z-axis or intensity signals. Display devices 33a, 33b may also be television receiver sets if the input signals are processes through a video scan converter.

The first display device 33a receives the same X and Y sweep frequency signals, from generators 24 and 27, that are applied to the scanning X-ray source 12. The output signal of the first detector 13a are applied to the Z or intensity signal terminal of first display device 33a through a preamplifier 36a at the detector and a primary amplifier 37a. Thus as the X-ray origin point 19 at source 12 is swept through a raster scan 22, an image corresponding to the raster scan is generated at the screen 34 of first display device 33a in which the brightness of successive points along the imaged raster scan varies in accordance with variations of X-ray intensity at detection point D1 as the X-ray origin point passes along corresponding successive points in the course of the raster scan.

The second display device 33b enables the step of combining successive data values produced by one of the detectors 13a with successive data values produced by the other detector 13b a predetermined interval later during the course of the raster scan 22 as previously described. In particular, the image generated by second display device 33b during the course of the raster scan 22 is shifted a predetemined distance along one coordinate axis, the Y axis in this example, relative to the image being concurrently generated by the first display device 33a. Superimposing the positionally shifted image of second display device 33b with the unshifted image of first display device 33a, as will hereinafter be discussed in more detail, is then in effect a combining of data values of the type discussed above.

In order to shift the image at second display device 33b, the X sweep frequency signal from generator 24 is applied to the second display device in the same direct manner that it is applied to the first display device 33a but the Y sweep frequency signal from generator 27 is modified before being applied to the second display device. In particular, the Y sweep frequency from generator 27 is applied to the second display device 33b through one input of a summing amplifier 38. The other input of the summing amplifier 38 is provided with a selected D.C. voltage from the adjustable tap of a potentiometer 39 which is connected across a direct current voltage source 41.

Summing amplifier 38 adds the selected fixed voltage to the Y sweep frequency voltage causing the position of the image at the screen 34 of second display device 33b to be shifted upward relative to the position of the image at the screen of the first display device 33a. The distance that the image is shifted is a function of the magnitude of the D.C. voltage that is added to the Y sweep frequency voltage and determines the particular plane 31a that will be depicted in the tomographic image.

Output signals from detector 13b are transmitted to the Z or intensity signal terminal of second display device 33b through a second preamplifier 36b and primary amplifier 37b. Consequently, the shifted image exhibits brightness variations indicative of variations of X-ray intensity at a detection point D2 during the course of the raster scan 22 but a given point in the raster scan, such as point C is imaged at a higher location at the screen 34 of display device 33b than it is at the screen of display device 33a.

While the image at one of the display devices 33b is shifted upwardly in this example, tomographic images may also be produced by shifting the image at either display device 33 in either direction relative to the image at the other display device by adding a D.C. voltage of appropriate polarity to the Y sweep frequency signal that is supplied to the device at which the image is to be shifted. While the image at one of the display devices 33 is shifted in the Y coordinate direction in this example, it is also possible to shift the image in the X coodinate direction at either display device by adding a D.C. voltage from a potentiometer 39 to the X sweep frequency voltage at the device at which the image shift is desired although this requires that the detection points D1 and D2 be spaced apart in the X-coordinate direction of the raster scan 22.

The desired tomographic image of the selected plane 31a is produced by superimposing the images at display devices 33a and 33b in register with each other as they appear on the screens 34 of the devices. Optical devices which combine two separate images for direct viewing may be used or, as in this example, a permanent tomographic image may be produced by photographing the images at the two screens 34 at one half of the normal exposure. The camera or cameras 42 are identically positioned at the two screens 34, normally in centered relationship to the screens. To facilitate registering of the two images during the printing operation, indicia marks 43 may be provided in identical positions on the two screens 34.

Referring now to FIG. 2, the developed negatives 44a and 44b obtained from the photographing operation will each have one half of the normal contrast. One of the negatives 44a is then disposed against unexposed print film 46 and is contact printed using a light source 47 and conventional printing techniques. Negative 44a is then removed and the other negative 44b is identically positioned against the print film 46 and is similarly contact printed on the once already exposed film 46. Developing of film 46 produces a permanent normal contrast image, shown in FIG. 3, which is the sum of the images that were generated at the screens 34 of the display devices 33a and 33b of FIG. 1 and which is a tomographic view of the selected plane 31a of the subject 32.

To facilitate understanding of the operation of the apparatus, the subject 32 as depicted in FIG. 1 is a simple sphere of uniform density or X-ray absorbency except at two minute internal points P1 and P2 at which relatively dense inclusions are present, point P1 being at the hypothetical plane 31a and point P2 being at a different hypothetical plane 31b that is closer to the X-ray source 12. Most subjects in medical, dental or industrial radiology have a more complex internal structure and it should be understood that what is herein described with respect to the imaging of the single points P1 and P2 is equally applicable to other points within the same planes 31a and 31b or other selected planes if there are density variations at such other points.

In operation, X-rays are emitted in all directions from the moving origin point 19 but only those X-rays traveling in a single direction influence the output signal from a particular detector 13a or 13b at any given moment. A particular point in the subject 32 such as point P1 affects the signal from a particular detector such as detector 13a only at one particular time in the course of a raster scan 22. Given the relative proportions and spacings of the source 12, subject 32 and detection poitns D1 and D2 shown in FIG. 1 for purposes of example, point P1 affects the signal from detector 13a only when origin point 19 is at position A in the raster scan 22. At that moment, but not at others, point P1 is situated in the X-ray path A-D1 from source 12 to detection point D1. Point P1 affects the signal from the other detector 13b only at a different and later time in the raster scan 22, specifically when the origin point 19 has been traveled to position C. Point P1 is then momentarily in the X-ray path C-D2 from the source 12 to detection point D2.

Thus both detectors 13a and 13b momentarily detect the dense inclusion at point P1 of the subject 32 but at different times in the course of the raster scan 22. The time interval which elapses while the origin point 19 traverses the successive scan lines from position A to position C will be herein termed T1.

The signal data produced by detector 31a when origin point 19 is at position A is not only determined by point P1 but also by other points within the subject situated along path A-D1. The signal data later produced by detector 13b when the origin point 19 is at position C is not only determined by point P1 but also by other points situated along X-ray path C-D2. Only point P1 affects the signal data in both cases. Consequently, if the signal data produced by the two detectors 13a and 13b at the two different times described above are combined or added, the resulting composite signal data is more strongly representative of density at point P1 within the subject 32 than of density at any other point along paths A-D1 and C-D2. The effect of point P1 on the composite data is twice that of any other point. The influence of point P1 in determining the magnitude of value of the composite data can be increased and the influence of other points may be further suppressed by adding in data obtained from additional detectors at still different times in the raster scan 22 as will hereinafter be described in more detail.

The operations described above for obtaining composite signal data that emphasizes point P1 are also applicable to all other points in plane 31a. Each successive signal data values from detector 13a may be added to the particular increment of signal data produced by detector 13b after the predetermined time interval T1 has elapsed. This results in sequential composite data values, during the course of the raster scan, that are indicative of variations of density between successive points within the plane 31a at the subject 32. An image of the raster scan 22 in which the brightness or some other visible characteristic of successive points along the scan has been determined by the sequential composite data values is thus a tomographic image of plane 31a.

In the embodiment of FIGS. 1, 2 and 3 as previously described, the combining of successive increments of data originated by detector 13a with later originated successive increments of data from detector 13b occurs when photographic negatives 44a and 44b are contact printed on film 46. This operation can also be performed by digital data processing as will hereinafter be described.

Changing the extent to which the image at one of the display devices 33b is shifted relative to the image at the other display device 33a, by adjustment of potentiometer 39, results in the tomographic imaging of a different plane within the subject 32. For example, point P2 in FIG. 1 lies in a plane 31b that is closer to the X-ray source 12 than plane 31a. Point P2 only affects the output of detector 13a when the X-ray origin point 19 is at position E in raster scan 22 and only affects the output of detector 13b at the later time when the origin point is at position F. The timer, herein termed T2, required for the origin point to travel from position E to position F is one half of the time T1 required for the origin point to travel from position A to position C.

Thus point P2 and other points in the plane 31b can be emphasized in the tomographic image by reducing the upward shift of the image at display device 33 to one half of that used to produce the tomographic image of plane 31a. Under that condition each signal data values from detector 13a is combined, in the tomographic image, with the signal data value from detector 13b produced time T2 later in the course of the raster scan 22 causing points in the plane 31b to be more strongly depicted in the tomographic image for reasons similar to those previously described with respect to the imaging of plane 31a.

Other selected planes in the subject 32 may be tomographically imaged in essentially the same manner by varying the amount by which the image at one display device 13a, 13b is shifted relative to the image at the other display device. In general, increases in the degree of shift result in tomographic images of planes which are progressively further from the X-ray source 12.

In a variation of the method, tomographic images of selected planes such as 31a or 31b may be produced without shifting the image displayed at one device 33a, 33b relative to the image displayed at the other such device as the shifting step can be accomplished during the photographic printing operations. In particular, potentiometer 39 can be adjusted to deliver zero voltage to summing amplifier 38 or the potentiometer, summing amplifier and voltage source 41 may simply be eliminated from the circuit. The tomographic imaging apparatus may then be operated in the manner previously described except insofar as the raster scan image at display device 33b will not be vertically displaced relative to the image at display device 33a. Point C, for example, will appear at the same location on the two screens 34. Refering again to FIG. 2, photographic negatives 44a and 44b of the two display device images may again be printed on contact paper 46 in the manner previously described except that one of the negatives 46b is shifted upward, as shown in dashed lines in FIG. 2, relative to the location of the other negative 46a during the printing exposure.

If the upward displacement of negative 44b corresponds to the image displacement that was accomplished electronically in the previously described embodiment of the method, then development of contact paper 46 produces the same tomographic image as the previously described embodiment and which is depicted in FIG. 3.

In the photographic printing operations hereinbefore described, exposures of the two negatives 44a and 44b are made in sequence. Alternately, both negatives 44a and 44b may be positioned at contact paper 46 at the same time and may be jointly printed by a single operation of the light source 46. In a simultaneous exposure of this kind slightly better definition in the tomographic image may be realized by locating the depicted source 47 of divergent light further away from the negatives 44a, 44b or by replacing it with a broad source of parallel light rays. Light absorption in the negative 44a, 44b which is closest to the source 47 may tend to suppress some data from the following negative but this is not necessarily a serious problem in all instances.

Referring again to FIG. 1, it has been hereinbefore pointed out how a particular single point P1 in the selected plane 31a becomes emphasized in the tomographic image while points such as P2 that are away from that plane are de-emphasized. From geometrical considerations, with reference now to FIGS. 4 and 5 in conjunction, it may be seen that all other points in the same plane 31a, such as P3 and P4 for example, are emphasized for similar reasons. P3 represents a point in the plane 31a that is offset downwardly from P1 an arbitrary distance and P4 represents a point in the same plane offset from P1 in the horizontal or X-axis direction.

Referring to FIG. 5 in particular and as previously pointed out, point P1 affects X-ray intensity at detection point D1 only when the X-ray origin port 19 is at position A at the face 18 of the X-ray source and only affects detection point D2 at the particular later time when the origin point has traveled to position C. The downwardly offset point P4 in plane 31a affects D1 only at a later moment when the origin point 19 has traveled to a lower position E and affects D2 only after still further travel of the origin point to position G.

As is evident from FIG. 5, the distance E-G, from position E to position G, is the same as the distance A-C, from position A to position C, and clearly the relationship holds for any other arbitrarily chosen point P5 situated directly above or below point P1 within plane 31a. The origin point 19 must travel a predetermined constant distance equal to A-C after detection of such an arbitrary point P5 before the same point is detected at D2. The raster sweep speed of X-ray origin point 19 is constant and thus a constant time interval hereinbefore termed T1 is required for the origin point 19 to travel that predetermined constant distance. Thus in each data value from D1 is combined with the data value originating from D2 time interval T1 later, the influence of points such as P1, P3 and P5 on the composite data is twice that of points located at other planes within the subject.

Lines A-C and E-G remain equal and thus time interval T1 remains the same if the several ray paths A-D1, C-D2, E-D1 and E-D2 of FIG. 5 are visualized as being rotated out of the plane of the drawing about the axis defined by line D1-D2. Thus, with reference to FIG. 4, time interval T1 remains the same for points in the selected plane 31a such as P4 that are offset from point P1 in the horizontal or X-axis direction.

Accordingly, with reference again to FIG. 1, the amount by which the image at display 33b is shifted relative to the image at display 33a is the distance A-C if the raster scans at X-ray source 12 and devices 33a and have the same size. If there is a difference in the sizes of the raster scans, then the amount of the shift is equal to $(A-C) \times H1/H2$ where H1 is the height of the raster scan at source 12 and H2 is the height of the raster scans at the display devices 33a, 33b.

The specific numerical value for distance A-C in a particular imaging system 11 is itself determinable from geometrical relationships apparent in FIG. 5. From the laws of similar triangles, distance A-C may be seen to be equal the distance between detection points D1 and D2 multiplied by the factor L1/L2 where L1 is the spacing of the selected plane 31a from the target plate 18 of the X-ray source and L2 is the spacing of the selected plane from the detection points D1 and D2. The previously referred to time interval T1 that is required for the X-ray origin point 19 to travel the distance A-C in the Y axis direction in a particular imaging system 11 may be expressed as a specific numerical value by dividing the distance A-C by the total height of the raster scan at the X-ray source 12 and multiplying the result by the duration of an individual raster scan.

Factors which determine the degree of shifting of one image data set relative to the other have been discussed above, for purposes of example, with reference to an imaging system 11 in which the detection points D1, D2 are spaced apart in the vertical or Y axis direction and thus the image shift takes place in that direction. Similar considerations apply to systems having detection points D spaced apart in the horizontal or X-axis direction and in which the image shifting is done in that direction except that reference to the heights of the raster scan in the foregoing discussion should in this case be read as references to the width of the raster scans and references to the duration of raster scans should be read as references to the duration of one line scan.

Time intervals T1 are substantially smaller in the case of horizontal shifts of image data from a detection point D as the X-ray origin point travel much more rapidly in the X axis direction than in the Y axis direction.

Referring again to FIG. 4, an embodiment will be hereinafter described in which image data obtained from a larger number of detection points, such as points D1 to D7 for example, is positionally shifted and combined to produce the tomographic image. The image from each additional detection point D3 to D7 requires a different horizontal and/or vertical shift which may be determined by the procedure described above with respect to shifting of the image data from point D2 in particular. Such shifts bring the images generated from each of the additional detection points D3 to D7 into the proper register with the unshifted or reference image from detection point D1 that is needed to produce the tomographic image in the manner previously described.

For example, images from detection points D1 to D7 having the relative locations shown in FIG. 4 may be brought into register by the shifts shown in FIG. 6. In FIG. 6, the shift distance for bringing the image from point D2 into register with the image from point D1 as determined for the particular system in the manner previously described is assigned a numerical value of one. Positive numbers designate an upward shift of the image as viewed on the screens 34 of the display devices 33 of FIG. 1 and negative numbers indicate a downward shift in the case of the vertical shifts (dy). Positive numbers indicate a shift to the right on the screens 34 of the display devices 33 and negative numbers indicate a shift to the left in the case of the horizontal (dx) shifts.

FIG. 6 represents the image shifts in terms of distance and thus the shifts are equal to one or multiples of one, given the arrangement of the detection points D1 to D7 in rows and columns with equidistant spacing that is shown in FIG. 4. The X-ray origin point travels a distance dx in the horizontal direction in less time than it travels a similar distance dy in the vertical direction. Thus to express the shifts shown in FIG. 6 in terms of raster scanning time (T) it is necessary to multiply the values shown for dy in particular by the factor $V_x/V_y$ where $V_x$ and $V_y$ are the horizontal and vertical sweep frequencies respectively. That factor is equal to the number of scan lines in the raster scan.

Referring again to FIG. 1, the invention was described initially with respect to a tomographic imaging system 11 having two detectors 13 to facilitate an understanding of the basic principles of operation. Tomographic images produced by such a system 11 are useful for some purposes as detail from the selected plane 31a is strongly emphasized but, under most conditions, a background and foreground of data from other planes may be visible to some extent. Systems 11 having a larger number of detectors 31 more fully suppress data from planes other than the selected plane 31a. Visible data from other planes may as a practical matter be virtually suppressed from the tomographic image by combining data from a sufficiently large number of detectors 13.

To avoid obscuring basic elements, the apparatus of FIG. 1 was depicted without certain auxiliary components that are advantageous in many instances although not essential in all usages. Referring now to FIG. 7, these include X-ray absorbent shielding 51 positioned to absorb X-rays which may approach the detector or detectors 13 from directions other than that of the X-ray source 12. Such X-rays can otherwise introduce spurious information into the tomographic images. Preferably, each detector 13 is also shielded from the other detectors. For example, if there are four detectors 13 as shown in FIG. 7 the shielding 51 may include a cylindrical shield portion 52 encircling all four detectors and which contains a cross shaped internal portion 53 extending between each detector and the other detectors. The internal portion 53 suppresses cross talk from inter-detector X-ray scattering.

It is also advantageous in many instances to dispose a multi-apertured collimator 54 between the X-ray source 12 and the subject 32, preferably against the face 18 of the source. The collimator 54 may be of the laminate type described in my prior U.S. Pat. Nos. 4,288,697 and 4,465,540 or the lead glass fiber type described in my prior U.S. Pat. No. 4,196,351 which have an X-ray absorbent body 56 transpierced by an array of minute, closely spaced radiation transmissive passages 57 each of which is directed towards the region occupied by the several X-ray detectors 13.

A collimator 54 of this kind absorbs X-rays which the source 12 would otherwise emit in the general direction of the subject 32 but which are not directed towards the detectors 13 and therefore would not contribute useful information to the desired image. This reduces radiation exposure of the subject 32 as is particularly important in medical or dental usage and also reduces the undesirable effects of scattered X-rays on image quality that occur in radiology operations in general.

In instances where radiation exposure of the subject 32 is to be minimized and/or image degradation is to be minimized, the detectors 13 are preferably positioned as close together as the constraints imposed by shielding 51 will permit. Collimator 54 may be of the type having slightly convergent X-ray passages 57 to define an X-ray focal region 58 extensive enough to enable X-rays from each passage to reach any of the detectors 13 but which is preferably no more extensive than is necessary for that purpose. X-ray paths which do not pass through both the subject 32 and the array of detectors 13 cannot contribute useful information to the tomographic images but can increase the scattered X-ray background with resulting adverse effects on the images. The spacing of subject 32 and detectors 13 from source 12 may be varied and collimators 54 having different degrees of focussing may be used to maintain the above described conditions when a series of subjects 32 have different sizes. A laminated collimator 54 of the kind described in my prior U.S. Pat. No. 4,288,697, in which the degree of focussing may be changed by changing lamination spacing, may also be used.

Referring again to FIG. 1, the tomographic imaging apparatus 11 depicted therein may in some instances be operated on the basis of a single raster scan 22 if the display devices 33a and 33b have sufficient persistence to retain the images at screens 34 for a period sufficient to enable photographing of images at the screens as previously described. Repetitive raster scanning may also be used particularly if a single raster scan does not provide sufficient definition in the image.

The apparatus has been hereinbefore described in connection with the production of a tomographic image of a single plane 31a or 31b within the subject 32 during a single X-ray exposure. The information needed for imaging other planes is in fact generated during the single X-ray exposure and is present on the screens 34 of display devices 33a and 33b. Tomographic images of other planes may be produced by repeating the photographic printing operations which have been described with reference to FIG. 2 but with one of the negatives 44b shifted, in the Y-coordinate or vertical direction in this particular example, relative to the position which the other negative 44a occupies against print paper 46 during the contact printing operations. The amount of shifting of the one negative 44b determines the particular plane which will be emphasized in the developed print 46 of FIG. 3 in accordance with the plane selection principles which have been hereinbefore described. Images of additional planes may also be produced from a single X-ray exposure by connecting additional duplicate analog data processing systems 14 to the detectors 13 of FIG. 1 with the potentiometer 39 of each such system adjusted to produce a different amount of shift or displacement of the image at one display device 33b of each system. Photographic prints made from the data provided by each such system 14 in the manner previously described then constitute a series of tomographic images 46 depicting the different planes.

Tomographic images can be produced more easily and quickly by replacing the analog data processing system 14 of FIG. 1 with a digital data processing system 14a such as that depicted in circuit form in FIG. 8. A digital data processing system 14a can also provide greater flexibility with respect to the kinds of tomographic image that can be produced.

Referring momentarily to FIGS. 1 and 8 in conjunction, the amplified detector output signals from amplifiers 37a and 37b may be applied to first and second input terminals 61a and 61b respectively of the digital data processing system 14a. X and Y sweep frequencies for establishing the scanning movement of the X-ray origin point 19 at X-ray source 12 are generated by the digital system 14a in this embodiment, in a manner to be described, instead of by the free running generators 24 and 27 of the previously described embodiment.

Referring now to FIG. 8 in particular, the first detector signals applied to first input terminal 61a are transmitted to a first analog to digital signal converter 62a through an integrating circuit 63a. Integrating circuit 63a includes a resistor 64a connected between input terminal 61a and the input 65a of converter 62a and a capacitor 67a connected between input 65a and ground. At least one of the resistor 64a and capacitor 67a is preferably adjustable to enable adjustment of the time constant of the integrating circuit 63a. This provides for selection of different degrees of signal integration in order to emphasize different aspects of the subject in an image. Increasing the time constant increases the contrast in the image between regions of the subject of different densities but diminishes the sharpness of the boundaries between such regions. A lower time constant diminishes contrast but emphasizes edges of such regions.

The second detector signals at second input terminal 61b are similarly applied to input 65b of another analog to digital signal converter 62b through another similar integrating circuit 63b.

Converters 62a and 62b, which produce four bit digital output signals in this example of the system 14a, are coupled to first and second random access memories 66a and 66b respectively through first and second four channel data buses 70a and 70b respectively. Repetitive, positive clock signal pulses from a horizontal clock circuit 68 are transmitted to converters 62a and 62b and are transmitted to random access memories 66a and 66b through a signal inverter 69. In response to the leading or positive edge of each clock pulse, converters 62a and 62b operate in the known manner to generate four bit binary signals that identify the momentary magnitudes of the voltages at inputs 65a and 65b respectively. The negative or trailing edge of each clock pulse then causes inverter 69 to transmit a positive going write pulse to memories 66a and 66b to write the digital output signals of converters 62a and 62b into memories 66a and 66b respectively together with an address location which identifies the location in the raster scan at which the set of signals originated.

To generate the digital signals which represent the address location, the clock pulses from clock circuit 68 are transmitted to a five bit horizontal counter register 71. The five bit digital signal output of counter register 71 identifies, at any given moment during the scanning of a raster line, the number of clock pulses which have been received and thus the momentary position of the X-ray origin point along the raster scan line. A five channel X-address bus 72 is coupled to the output of counter register 71 to transmit the X address signal bits to other components of the system 14a to be hereinafter described.

Y or vertical address digital signals are generated by a second counter register 73 having an input coupled to the fifth output channel 74 of the first counter register 71 through a scale of two binary flip-flop 76. The first counter register 71 is of the form which resets to zero after 32 counts have been received and in which the final output channel 74 goes positive twice in the course of registering the 32 counts. Thus owing to the scale-of-two flip-flop 76, one count is transmitted to the second counter register 73 each time that the first counter register 71 resets to zero. The output of second counter register 73 is transmitted to other components of the system 14a as will be hereinafter described through a five channel Y-address bus 77.

The X-address signal bits from bus 72 which are stored by memory 66a in conjunction with storage of each set of detector signal bits from converter 62a are transmitted to the memory through a first adder 78. Adder 78 enables selective modification of the X address signal values in a manner to be hereinafter described and for this purpose a first switch register 79 is coupled to the adder. Switch register 79 is of the form which may be set to transmit a selected count value, in five bit binary form, to adder 78 for combination with the X address count values that the adder receives from bus 72

In an essentially similar manner, Y address signals from bus 77 are transmitted to the first memory 66a through another adder 81 which may add a selected count value to such signals from another switch register 82.

X address signals are provided to the second memory 66b through another adder 83 which receives count values from both bus 72 and another switch register 84. Still another adder 86, receiving count values from bus 77 and another switch register 87, transmits Y address signals to the second memory.

In this embodiment of the invention, sweep signals for producing the raster scanning action at the X-ray source are generated from the digital output signals of counter registers 71 and 73. In particular, a digital to analog signal converter circuit 88 is coupled to the X address data bus 72 and another similar circuit 89 is coupled to the Y address data bus 77. Thus converter circuit 88 produces a voltage that repetitively rises with the repetitive rises of the clock pulse count at the horizontal counter register 71 while converter circuit 89 produces a voltage that rises more slowly in accordance with the increasing count value registered by the vertical counter register 73. The output voltage of converter circuit 88 is transmitted to the previously described X sweep frequency terminal 26 of the X-ray source through a buffer amplifier 91 and the output voltage of converter circuit 89 is transmitted to the Y-sweep frequency terminal 28 of the X-ray source through another buffer amplifier 92. Thus, with reference again to FIG. 1, the X-ray origin point 19 is traveled along successive scan lines 23 at a rate determined by the frequency of the clock signal circuit 68 of FIG. 8.

Referring again to FIG. 8, the X and Y sweep voltages produced by digital to analog converter circuits 88 and 89 respectively are also transmitted to the X and Y sweep frequency terminals 93 and 94 of an oscilloscope 96 or other display device that is used to display the tomographic images as will hereinafter be described in more detail. Thus the raster scanning patten at the screen 97 of display device 96 is similar to and synchronized with that of the X-ray origin point at the X-ray source.

With reference again to FIGS. 1 and 8 in conjunction, if switch registers 79, 82, 84 and 87 are each set to a count of zero while the X-ray source 12 completes a raster scan, adders 78, 81, 83 and 86 will transmit unmodified X and Y address locations to random access memories 66a and 66b for the successive digitized X-ray intensity signals that are stored in the memories. At the completion of the raster scan under that condition, memory 66a will have stored X-ray count values for successive locations along the raster scan as obtained from detection point D1. Memory 66b will have stored similar data as obtained from the spaced apart detection point D2. In effect, each memory 66a and 66b will have stored data from which a non-tomographic X-ray image of the subject 32 can be constructed, such images being taken from spaced apart viewpoints D1 and D2.

In accordance with the method for producing a tomographic image as previously described, the image data stored in one memory 66a or 66b must in effect be shifted relative to the image data in the other memory, by an amount dependent on the selected plane within the subject that is to be emphasized, and then be combined with the image data from the other memory for display. This is accomplished by entering a selected address offset value into a least one of the switch registers 79, 82, 84, 87.

If, for example, a given binary number is set into switch register 87 then adder 86 adds that value to the Y address signals that are transmitted to memory 66b. Thus the Y address locations of the X-ray counts being stored in memory 66b are each changed by a fixed amount relative to the Y address locations of counts that are being concurrently stored in the other memory 66a.

To generate a tomographic image at display device 96, the data set stored in memory 66a is added to the offset data set stored in memory 66b by a five bit plane adder 98 and the resulting summed image data set is then stored in a five bit plane random access memory 99. The output of memory 99 is coupled to the Z or intensity signal terminal 101 of display device 96 through another digital to analog converter 102. Thus upon readout of the data stored in memory 99, converter 102 applies a voltage to the display intensity signal terminal 101 that varies in accordance with variations between successive X-ray count values of the summed data set. Thus device 96 displays an image in which the characteristics of a specific plane within the subject are emphasized in accordance with the principles which have been hereinbefore described.

As previously described, offsetting of one X-ray image relative to the other prior to combining the two images to produce the tomographic image may in some cases be in the X axis direction instead of in the Y axis direction as in the example described above. This may be accomplished by entering the desired offset value into switch register 84 instead of switch register 87. Similarly, if it is desired to offset or shift the image data in memory 66a instead of the data in memory 66b, the offset value may be entered into either switch register 79 or 82 depending on whether the offset is to be in the X axis or the Y axis direction.

It may be observed from the foregoing that it is only necessary to make use of a single one of the switch registers 79, 82, 84, 87 in order to produce a tomographic image in a two detector system as depicted in FIG. 8. The additional switch registers 79, 82, 84 and 87 provide the capability of entering X and/or Y address offsets to the detector signal values stored in any of the random access memories 66a, 66b and thereby provide for the processing of data from additional detection points as previously described with respect to FIGS. 4 and 6. As shown in FIG. 4, the X-ray detection points D1 to D7 are spaced from each other in the X and/or Y coordinate directions. Thus the X-ray count values originating from each detection point D1 to D7 require a different address offset before being combined in the final random access memory 99 of FIG. 8. FIG. 9 depicts additional components which may be added to the circuit for this purpose. Portions of the circuit which are not shown in FIG. 9 may be as previously described with respect to FIG. 8.

Referring to FIG. 9, the random access memories 66a and 66b which store data from detection points D1 and D2 as previously described are supplemented with additional similar memories 66c to 66g which respectively store X-ray count values from detection points D3 to D7. Components which input X-ray count values and address locations to each of the additional memories 66c to 66g may be similar to those previously described with reference to memory 66a and thus, with reference to FIG. 8, include an integrating circuit 63a, analog to digital signal converter 62a, X-address input adder 78 with switch register 79 for selectively entering an address offset and Y address input adder 81 with switch register 82 for selectively entering an address offset.

Referring again to FIG. 9, a particular detection point, D1 in this example, is selected as the reference detection point and no address offset is added into either the X or Y addresses that are stored in the associated memory 66a. Given the relative positions of the detection points shown in FIG. 4, Y address locations applied to the second memory 66b are each increased by a fixed amount which is arbitrarily designated as +1 in FIG. 9 but which is determined by selection of the plane in the subject 32 that is to be imaged as has been previously described. X address locations applied to the second memory 66b are unmodified as detection point D2 is directly above the reference detection point D1. Both the X and Y address locations applied to the third memory 66c are increased by +1 as point D3 is above point D1 by the same amount as point D2 and is also offset to one side of point D1 by a similar distance. X and Y address offsets for the additional memories 66d to 66g are adjusted in accordance with the same principle to bring all of the stored image data sets into the desired registration and, in the present example, are as shown in FIGS. 6 and 9.

The image data set stored in memory 66a is combined with the offset image data set stored in memory 66b by adder 98 as previously described. The data sets in memories 66c and 66d are combined by another adder 104 and the data sets in memories 66e and 66f are combined in still another adder 106. The outputs of adders 98 and 104 are then combined in another adder 107 and the output of adder 107 is itself combined with that of adder 106 by still another adder 108. A final adder 109 combines the data set stored in memory 66g with the output of adder 109.

Thus the final adder 109 transmits a composite data set which is the summation of the mutually offset data sets of memories 66a to 66g. The composite data set from addder 108 is stored in random access memory 99 for readout to display device 96 through digital to analog signal converter 102 to produce the tomographic image in the manner previously described.

The circuit of FIG. 9 has been described for purposes of example in a form which processes data from seven detection points D1 to D7. The circuit may be adapted to combine data from differing numbers of detection points by increasing or decreasing the number of random access memories 66 and associated components.

Referring again to FIG. 1, the previously described methods and apparatus produce tomographic images of planes 31a, 31b, herein termed XY planes, that are parallel to the target plate 18 of the X-ray source 12. If point by point image data for a series of such XY planes is obtained and stored with the hereinbefore described techniques, then the stored data may also be used to produce tomographic images of differently oriented planes within the subject 32 and also non-planar sectional views of the subject such as curved section views. FIG. 10 depicts a modification of the digital data processing system of FIG. 8 that enables production of such images.

Dashed lines 111 of FIG. 10 encloses additional components which are linked to the final random access memory 99 in a manner which will now be described to accomplish the above described results. To facilitate an understanding of the operation of the additional components, certain of the previously described components of the circuit of FIG. 8 are redepicted in FIG. 10 outside dashed line 111. All other portions of the circuit, not shown in FIG. 10, may be as previously described with reference to FIG. 8.

Memory 99 operates in the manner previously described to store an image data set, received from adder 98, which defines a tomographic image of a first selected XY plane. Such image data set may be derived by combining X-ray counts from two detection points as described with reference to FIG. 8 itself or from combining of counts from a larger number of detection points if the previously described circuit components of FIG. 9 are included in the system.

Referring again to FIG. 10, memory 99 is supplemented in this embodiment by an additional series of random access memories 112a to 112d which function as buffer storage for a series of additional image data sets produced in the previously described manner but which are each descriptive of a separate one of a series of closely spaced apart XY planes within the subject. The number of memories 99, 112a to 112d that are provided corresponds to the number of pixels that will be present in the tomographic image along the Z axis which is the axis that is mutually perpendicular to the X and Y axes of the system as hereinbefore defined. Only five such memories 99, 112a to 112d are shown in this example to reduce complication in the drawings but in most cases it is preferable to provide a larger number to produce images that are more extensive in the Z axis direction.

X and Y address locations for successive X-ray count signals are transmitted from the X and Y counter registers 71 and 73 to memory 99 in the manner previously described except that switches 113 and 114 are present in the X and Y address buses 72 and 77 respectively to enable substitution of other address signals during readout for purposes to be hereinafter described. The X and Y address locations and the X-ray count values are also transmitted to each of the other memories 112a to 112d.

Clock pulses from clock circuit 68 and inverter 69 are transmitted to only one of the memories 99, 112a to 112d at any given time so that only one of the memories operates to store an image data set at that time. For this purpose a switch 116 receives the clock pulses from inverter 69 and has six positions, the first of which is an open position. Switch 116 transmits the clock pulses to a separate different one of the memories 99, 112a to 112d at each of the additional switch positions.

If switch 116 is positioned to apply the clock pulses to memory 99 in particular, the system may be operated in the manner previously described to store an image data set in that memory that defines a tomographic image of a first selected XY plane within the subject. Switch 116 is then set to the next switch position to enable data set storage in the next memory 112a while, with reference again to FIG. 8, a different Y or X address offset is entered into one or more of the switch registers 79, 82, 84, 87 in the manner previously described to select a second XY plane for imaging in the second tomographic image data set, the selected second XY plane being spaced at least slightly in the Z axis direction from the XY plane represented by the data set stored in the first memory 99.

Referring again to FIG. 10, a series of additional X-ray scannings of the subject are then performed in essentially the same manner with switch 116 being repositioned and with changed address offsets being entered between each such scanning. This stores additional data sets in the remaining memories 112b to 112d each of which defines a tomographic image of one of a series of successive spaced apart parallel XY planes within the subject.

The output of each memory 99, 112a to 112d is coupled to a separate successive input of a demultiplexer switch 117 which operates, at any particular moment, to transmit X-ray count values from a single one of the memories to the Z or intensity signal terminal 101 of the previously described display device 96 through digital to analog signal converter 102. X and Y sweep frequency signals are provided to display device 96 from counter registers 71 and 73 respectively through digital to analog converters 88 and 89 respectively as previously described with reference to FIG. 8.

Referring again to FIG. 10, the demultiplexer switch 117 is of the known form which is provided with a control input 118 to which digital address signals may be applied to select one of a plurality of devices, which are memories 99, 112a to 112d in this instance, for coupling to the display device 96 at any particular moment. To supply the address signals to control input 118 in a first mode of operation, a control switch 119 has a first position at which the control input 118 receives the Y address signals from vertical counter register 73. A second operational mode, to be hereinafter described is enabled by switching switch 119 to a second position at which address signals are received from a switch register 123.

Additional components used in the production of the tomographic images include five bit switch registers 124 and 126 which may be selectively coupled to the X address bus 72 and Y address bus 77 respectively by closure of switches 127 and 128 respectively.

A tomographic image of any one of the XY planes represented by data sets stored in the memories 99, 112a to 112d may be produced at display device 96 by setting the address of the particular memory into switch register 123 and positioning switch 119 to transmit that address to demultiplexer switch 117 over bus 130. Switch 116 is set to transmit clock pulses to the selected memory and switches 113 and 114 are closed to transmit X and Y address signals to memories 99 and 112a to 112d. Demultiplexer switch 117 then transmits the successive X-ray count values from the selected memory 99, 112a to 112d to display device 96 through digital to analog converter 102 to produce a tomographic image of the selected XY plane essentially in the manner previously described.

The system may also be operated or reoperated to generate tomographic images of XZ planes or YZ planes. Referring to FIG. 1, XZ planes contain or are parallel to both the X and Z coordinate axes of the system and thus are horizontal if the scanning apparatus 11 is oriented as depicted in the drawing. YZ planes contain or are parallel to both the Y and Z coordinate axes and thus are vertical but at right angles to planes 31a and 31b when the apparatus 11 has the depicted orientation.

To produce an image of a selected XZ plane, with reference again to FIG. 10, switch 116 is set to the open position so that none of the memories 99, 112a to 112d receive clock pulses. Switch 114 is opened to prevent transmission of the successive Y address locations from counter register 73 to the memories 99, 112a to 112b. The binary Y address of the selected XZ plane is set into switch register 124 and switch 127 is closed to transmit that constant Y address location to each of the memories 99, 112a to 112d throughout the readout of data for the XZ plane tomographic image. Switch 119 is positioned to transmit successive Y addresses from counter register 73 to the control input 118 of demultiplexer switch 117.

The initial Y address signal from counter register 73 sets demultiplexer switch 117 to read out data from from the first memory 99 to the display device 96. Thus the initial sequence of X address signals generated by counter register 71 causes the initial raster scan line to display device 96 to exhibit variations in intensity corresponding to variations of the X-ray count values stored in memory 99 at the selected fixed Y address that has been set into switch register 124. A the end of that sequence of X address signals, the vertical counter register 73 generates a second Y address signal in the manner which has been previously described. The new Y address signal is transmitted to display device 96 to cause display of a second raster scan line but is not transmitted to any of the memories 99, 112a to 112d as switch 114 is open. The memories 99, 112a to 112d continue to receive the fixed Y address that was set into switch register 124.

Through the switch 119, this second Y address signal is received at the control input 118 of demultiplexer switch 117. This conditions the demultiplexer switch 117 to disconnect from memory 99 and to transmit data read out from the next memory 112a instead. Consequently, the next raster scan line at the display device 96 is indicative of the X-ray count values that are stored in the second memory 112 at the selected fixed Y address. In a similar manner, the next Y-address signal from counter register 73 sets the demuliplxer switch 117 to read out data for the following scan line at display device 96 from the next memory 112b at the selected fixed Y address. This process continues until successive scan lines at display device 96 have been generated from each of the remaining memories 112c, 112d in a similar manner. Demultiplexer switch 117 and counter register 73 are then reset to the initial Y address and the above described sequence of operations is repeated to maintain the image at display device 96.

The above described process is essentially one of abstracting data that lies along corresponding single lines in each of the XY plane data sets stored in memories 99, 112a to 112d and displaying such lines in sequence in order to depict an XZ plane that is perpendicular to the XY planes themselves.

The number of pixels (picture elements) that are present in the vertical direction in the tomographic image of the XY plane at the display device 96 is limited by the number of memories 99, 112a to 112d that are present in the apparatus. As previously pointed out, only five such memories 99, 112a to 112d are shown in FIG. 10 to avoid excessive complication in the drawing but more typically a substantially larger number of such memories is desirable to provide for imaging of a substantially larger number of scan lines at the display device 96. The additional memories may be interconnected with other components of the circuit in a manner similar to what has been described with respect to memories 99 and 112a to 112d. Switch 116 and the demultiplexer switch 117 are provided with a correspondingly larger number of switch settings to accomodate the additional memories, interconnections to such switch settings also being similar to those which have been described above.

The operations which have been described above with reference to FIG. 10 enable tomographic imaging of selected XZ planes within the subject. The same apparatus may be used to display tomographic images of other planes in the subject. Selected YZ planes may be imaged in an essentially similar manner by reclosing switch 114 so that Y address signals are again transmitted to the memories 99, 112a to 112d and by opening switch 113 to block transmission of X address signals from counter register 71 to the memories 99, 112a to 112d. Switch 127 is opened to isolate switch register 124 from Y address bus 77. The constant X address of the YZ plane that is to be imaged is set into switch register 126 and applied to X address bus 72 by closure of switch 128. The circuit may then be operated in the manner previously described to produce a tomographic image of the selected YZ plane at display device 96.

Images of oblique planes and curved sectional depictions of the subject may be produced at display 96 by opening switches 113 and 114 to block both the X and Y address signals of counter registers 71 and 73 from the memories 99, 112a to 112d and substituting fixed X and/or Y addresses from switch registers 124 and/or 126 that are changed each time that the data read out from a particular one of the memories 99, 112a to 112d is completed. For example, an image of a slanting plane that is parallel to the X coordinate axis may be produced by applying a constant X address to the memories 99, 112a to 112d throughout the process while sequentially increasing the value of the applied Y address each time that read out from an individual one of the memories is completed. The fixed amount determines the slope of the imaged plane and the fixed X address determines the location of the plane. Sequentially decreasing the applied Y address between individual memory read outs images an oppositely inclined plane. Planes which are oblique with respect to both the X and Y coordinate axes may be imaged by progressively changing both the applied X address and applied Y address after read out from each individual memory 99, 112a to 112d in the series of memories.

Curved sectional images of the subject may be displayed by altering the applied X and/or Y addresses after the readout from each individual memory 99, 112a to 112d is completed by non uniform amounts. Depiction of some forms of non-planar sectional views of the subject may require a non-sequential readout of data from the series of memories 99, 112a to 112d or, in other words, selective control of the Z addresses during the readout in addition to the above described control of X and Y addresses. For example, it may be necessary to read out lines of data from memories 99, 112a and 112b in sequence and then to reverse the direction of progression of the readouts through the series of memories 99, 112a to 112d by then reading out additional lines of data, at different X and/or Y addresses from memories 112a and 99 in sequence. This may be accomplished by positioning switch 119 to connect switch register 123 to control input 118 of demultiplexer switch 117 and then utilizing the switch register to change the memory address applied to demultiplexer switch 117 after each memory readout as may be necessary for the purpose.

In general, it may be seen from the foregoing that it is possible to establish any desired relationship between the variables X, Y and Z during the image generation process, by changing the values entered in switch registers 124, 126 and 123 as necessary for the purpose between readouts of data from the several memories 99, 112a to 112d. Thus a tomographic depiction may be generated at display device 96 that is a sectional view having any desired configuration and location within the subject.

The digital circuits of FIGS. 8, 9 and 10 are designed specifically for performing image data processing operations involved in the production of tomographic images in accordance with the present invention. Referring now to FIG. 11, a general purpose computer 131 in conjunction with a commercially available digital image processor 132 may also be used to perform essentially similar operations.

The data processing means 14b of FIG. 11 has four detector signal input channels 133a, 133b, 133c and 133d and thus is particularly adapted to scanning apparatus which includes four detectors 13 such as has been described with respect to FIG. 7. Referring again to FIG. 11, the data processing means 14b may readily be adapted to a larger or smaller number of detectors by adding or eliminating such channels 133.

Each detector 13 is coupled to a separate one of the channels 133 and, within the digital image processor 132, each channel includes a slow-scan controller (SSC) 137a to 137d coupled to a separate one of a series of frame buffers (MFB) 136a to 136d through a separate one of a series of auxiliary bus inputs 138a to 138d.

A clock circuit 139 provides repetitive clock pulses to each of the slow-scan controllers 137. The clock pulses are also transmitted to an X-address counter register 142. Successive clock pulses define the beginning of each pixel (picture element) in time and each such clock pulse is counted by the X-address register 142 to generate a digital value identifying the X address of each pixel. After each sequence of pixels for a single scan line has been counted, the X-address counter register resets to zero and transmits a count of one to a Y-address counter register 143. When the total of such counts reaches a value corresponding to the total number of scan lines in the image, Y-address counter register 143 resets to zero and a new set of frames may be started.

Referring now to FIGS. 7 and 11 in conjunction, a digital to analog converter 144 produces a voltage proportional to the value stored in X-address counter register 142 which voltage is applied to the X-sweep frequency terminal 26 of the X-ray source 12. The Y sweep frequency terminal 28 of the X-ray source 12 receives a voltage produced by another digital to analog converter 146 that is proportional to the value stored in Y counter register 143. Thus the electron beam 17 of the X-ray source 12 is directed to successive X and Y addresses of the raster scan 22 at the face of the X-ray source.

The digital to analog converters 144 and 146, clock circuit 139 and X and Y address counter registers 142 and and 143 may, if desired, be similar in detail to the corresponding components of the digital circuit previously described with reference to FIG. 8. Referrng again to FIG. 11, suitable frame buffers 136 (manufacturer's identification MFB 512) with auxiliary buses 138 together with an arithmetic logic unit 147 (manufacturer's identification ALU 512), a display buffer 134 and an analog processor 148 (manufacturer's idenification AP 512) for transmitting image signals to a display device 149 are commercially available as a unit, identified as Model IP512 Image Processor, from Imaging Technology, Inc., Woburn, Mass., U.S.A.. Suitable slow-scan controllers 137 (identification SSC 512) with instructions for incorporation into the image processor 132 are available from the same manufacturer. The host computer 131, to which the image processor 132 is coupled may, for example be a Model MLZ91 computer as manufactured by Heurikon Corporation, Madison, Wis., U.S.A.

During the scanning operation, slow-scan controllers 137 respond to each clock pulse by generating a digital signal indicative of the momentary magnitude of the voltage at the input which voltage is determined by the momentary rate of X-ray detection at the associated detector. Whan an acquire signal is received from computer 131 each slow scan controller 137 responds to successive clock pulses by transmitting the digitized voltage values for successive pixels to the associated one of the frame buffers 136 through the associated auxiliary bus 138. X and Y address signals for each pixel are concurrently transmitted by the slow-scan controllers 137 to frame buffers 136 through buses 138. Thus, upon completion of a raster scan, successive address locations in the frame buffers 136 store values indicative of the X-ray counts received on input channels 133 at corresponding locations in the raster scan.

After storage of the data for a complete raster scan, starting address locations in all but one, 136a, of the frame buffers 136 are shifted in accordance with the principles which have been heretofore described to cause the X-ray count data from each point in the plane of the subject that is to be imaged to be at the same address locations in each frame buffer. These shifts are programmed into computer 131 which executes the shifts and then executes the additions of the frame buffer contents in conjunction with the arithmetic logic unit 147 which operates a video rates and which is coupled to each of the frame buffers 136 through a video bus 151. Video bus 151 transmits the data from buffers 136 to the arithmetic logic unit 147, where the additions are performed, and the resulting composite signal values are then stored in display buffer 134 through another video bus 152.

The arithmetic logic unit 147 is coupled to the analog processor 148 through still another video bus 153 and controls display of the tomographic image at video display monitor 149 in conjunction with the analog processor which converts the digital composite signal values to analog form and into video signals compatible with the display monitor.

More particularly, the IP 512 image processor 132 is configurable in a manner which enables the four frame buffers 136 to be addressable by computer 131 as a single large frame buffer 154 having 1024 address locations in both x and y as depicted diagrammatically in FIG. 12. The four frame buffers 136a, 136b, 136c and 136d of FIG. 11 each form of a quadrant, $A_1$, $A_2$, $A_3$ and $A_4$ respectively, of the composite frame buffer 154 of FIG. 12. Scroll and pan coordinates of the starting address of each of the quadrants $A_1$, $A_2$, $A_3$, $A_4$ are as shown in FIG. 12. Computer 131 may be caused to operate on any selected 512×512 pixel array in the composite frame buffer 154 by supplying the computer with the starting scroll and pan coordinates of the array which is to be operated on. Thus a shifted array may be produced by providing computer 131 with an appropriate starting address determined by the image offset procedures hereinbefore described with respect to other embodiments of the invention.

FIG. 13 is a program flow chart for the above described operations in which the shifted scroll coordinate is given by $s=d_1$ and the shifted pan coordinate is given by $p=d_2$. A designates the composite frame buffer 154 of FIG. 12 and B designates the display buffer 134 of FIG. 11. In the system initialization procedure the arithmetic logic unit 147, designated ALU in FIG. 13, is set up to perform the summation of the selected 512×512 pixel arrays of the composite frame buffer 154 and to store the result in display buffer 134 and the system is also initialized to display the contents of buffer 134 at monitor 149.

The embodiments of the invention have been described with reference to the production of tomographic or sectional images. The apparatus may also be used to produce non-tomographic X-ray images in instances where such images may be needed. The image appearing at either display device 33a, 33b of FIG. 1 is a non-tomographic X-ray image of the subject. The image data stored in any single one of the random access memories 66 of FIGS. 8 to 10 or in any one of the frame buffers 136 of FIG. 11 can also be displayed to provide a non-tomographic image. Non-tomographic images can also be produced by combining the data stored in two or more of the random access memories 66 or frame buffers 136 without address shifts although this introduces some loss of definition which is dependent on the spacing of the detectors at which the data originated. Where that can be tolerated, radiation exposure of the subject may be reduced as X-ray intensity may be decreased by a factor of two or more relative to what is needed to produce a non-tomographic image with a single detector scanning X-ray apparatus.

While the invention has been described with respect to certain specific embodiments, many variations are possible and it is not intended to limit the invention except as defined in the following claims.

I claim:

1. In a method of producing a tomographic image of a subject that includes the steps of generating X-rays at a moving origin point by directing a charged particle beam to a target surface, deflecting said charged particle beam to travel said origin point through a predetermined raster scan at said surface, detecting variations of X-ray intensity during the course of said raster scan at a plurality of spaced apart detection points situated at the opposite side of said subject from said origin point, generating a first sequence of data values that is indicative of variations of X-ray intensity at a first of said detection points at successive times during the course of said raster scan and generating at least a second sequence of data values that is indicative of variations of X-ray intensity at a second of said detection points at successive times during the course of the same raster scan, the improvement comprising:

combining successive individual data values of said first sequence that are generated by X-rays from successive particular locations in said raster scan with at least individual data values of said second sequence that are generated by X-rays from predetermined successive different locations in the same raster scan in order to produce a composite sequence of data values, and producing an image corresponding to at least a portion of said raster scan which depicts variations of the magnitude of successive data values of said composite sequence.

2. The method of claim 1 including the step of combining each data value of said first sequence with the data value of said second sequence that is generated a predetermined constant time interval later in the course of the same raster scan.

3. The method of claim 1 including the step of combining successive data values of said first sequence that are generated by X-rays from successive particular locations along said raster scan with successive data values of said second sequence that are generated by X-rays from another series of locations in a preselected fixed direction by a preselected fixed distance.

4. The method of claim 3 including the step of preselecting said fixed distance in order to produce a tomographic image of a specific selected plane within said subject.

5. The method of claim 1 wherein said X-ray origin point is traveled along a plurality of parallel raster scan lines, including the step of producing said sequence of composite data values by combining each first sequence data value that is generated by X-rays from a location along a particular scan line with at least the second sequence data value that is generated by X-rays from the corresponding location along another scan line.

6. The method of claim 1 wherein said X-ray origin point is traveled along a plurality of parallel raster scan lines, including the step of producing said sequence of composite data values by combining each first sequence data value that is generated by X-rays from a location along a particular scan line with at least the second sequence data value that is generated by X-rays from another location along the same scan line situated a fixed distance away along the scan line.

7. The method of claim 1 including the further steps of generating additional sequences of data values each of which is indicative of variations of X-ray intensity at a separate additional one of said detection points during the course of said raster scan, and producing said composite sequence of data values by combining individual data values of each of said additional sequences with said individual data values of said first and second sequences, the individual data values of said first and second and additional sequences that are combined to produce each composite data value being ones that are generated by X-rays at different locations in said raster scan which are selected to provide a tomographic image of a specific selected plane within said subject.

8. The method of claim 1 including the further steps of producing a first non-tomographic image of said raster scan which displays variations of the magnitude of data values of said first sequence during the course of said raster scan, producing at least a second non-tomographic image of said raster scan which displays variations of the magnitude of data values of said second sequence during the course of said raster scan, and producing said tomographic image by combining said non-tomographic images with one thereof being positionally shifted relative to the other in order to superimpose successive data values of said first sequence with successive data values of said second sequence that originated at different times in the course of the raster scan.

9. The method of claim 8 wherein said combining of said non-tomographic images includes preparing photographic negatives of each of said non-tomographic images and printing each of said negatives onto a single area of photographic print paper or the like.

10. The method of claim 1 wherein said composite sequence of data values is descriptive of a first planar area within said subject including the further steps of producing a plurality of additional composite sequences of data values each of which is descriptive of a separate one of a series of additional spaced planar areas within said subject that are parallel to said first planar area, and combining portions of each of said composite sequences of data values to produce a constructed composite sequence of data values that is descriptive of a differently oriented area within said subject.

11. The method of claim 1 including digitized and storing each value of said first sequence of data values together with an address which identifies the location of said X-ray origin point in said raster scan at the time that the value was generated, digitizing and storing each successive value of said second sequence of data values together with an address which identifies a location in said raster scan that is spaced a predetermined distance from the location of said origin point at the time that the value was generated, and producing said composite sequence of data values by adding each of a series of data values of said first sequence and the data value of said second sequence which has the same storage address.

12. The method of claim 1 wherein said image is produced by traveling a light origin point in a raster pattern corresponding to said raster scan at said target surface of said X-ray source and utilizing said composite sequence of data values to modulate a characteristic of the light emitted from said light origin point during the course of said raster pattern.

13. A method of producing a tomographic image of an area within a subject comprising the steps of:
traveling an X-ray origin point through a raster scan which includes a plurality of parallel scan lines,
detecting X-ray intensity during the course of said raster scan at a plurality of spaced apart detection points situated at the opposite side of said subject from said X-ray origin point and producing a plurality of signal sequences each of which defines a successive series of values that differ from each other in accordance with variations of X-ray intensity at an associated one of said detection points at successive times during the course of the same raster scan,
combining signal values from each of said sequences that originate at predetermined different times in the course of said raster scan to produce a sequence of tomographic image signal values, and
producing said tomographic image by traveling a light origin point through a raster scan similar to said raster scan of said X-ray origin point while modulating a characteristic of the light emitted at said light origin point in accordance with said sequence of tomographic image signal values.

14. In tomographic imaging apparatus having an X-ray source wherein a charged particle beam is directed to a target surface to generate X-rays at an X-ray origin point at said surface and which has beam deflection means for moving said origin point through a raster scan at said surface, a plurality of X-ray detectors which are spaced apart from said source and positioned to detect X-rays at separate detection points that are spaced apart from each other, said detectors including a first detector which transmits a first sequence of data values that is indicative of variations of X-ray intensity at a first of said detection points at successive times during the course of said raster scan and at least a second detector which transmits a second sequence of data values that is indicative of variations of X-ray intensity at a second of said detection points at successive times during the course of the same raster scan, the improvement comprising:
means for combining individual data values from said first detector that are generated by X-rays from successive particular locations in said raster scan with individual data values of at least said second sequence that are generated by X-rays from predetermined successive different locations in the same raster scan in order to produce a composite sequence of data values, and means for displaying an image corresponding to at least a portion of said raster scan which depicts variations of the magnitude of successive data values of said composite sequence.

15. Apparatus of claim 14 wherein said means for combining individual data values combines each of a series of data values from said first sequence with the data values of said second sequence that was generated a predetermined constant time interval later in the course of said raster scan.

16. The apparatus of claim 14 further including:
first data storage means for storing data values of said first sequence in an arrangement which identifies each value with the location of said X-ray origin point at the time the was generated,
second data storage means for storing data values of said second sequence in an arrangement which identifies each value with a location that is spaced a predetermined distance from the location of said X-ray origin point at the time the value was generated, and
wherein said means for combining individual data values adds each of a series of stored data values from said first data storage means to the stored data value from said second data storage means that is identified with the same location.

17. The apparatus of claim 14 wherein said detectors include still additional detectors which transmit additional sequences of data values each indicative of variations of X-ray intensity at a different one of said detection points during the course of said raster scan, further including means for combining an additional data value from each of said additional sequences with the combined data values of said first and second sequences, said additional data values being values which were originated by X-rays from predetermined different locations in said raster scan.

18. The apparatus of claim 14 further including:
first and second digital data storages of the form which store a plurality of digital values at individual successive addresses,
a first analog to digital signal converter connected between said first detector and said first digital data storage and a second analog to digital signal converter connected between said second detector and said second digital data storage,
means for changing the storage addresses of data values in at least one of said digital data storages,
wherein said means for combining data values includes a third digital data sotrage and a digital adder having input buses connected to said first and second digital data storages and having an output bus connected to said third digital data storage.

19. The apparatus of claim 18 wherein said means for displaying an image includes a display device of the form in which a light origin point is traveled through a raster scan and which has means for modulating a characteristic of the light emitted from said light origin point and further includes a digital to analog signal converter connected between said third digital data storage and said means for modulating a characteristic of the light.

20. The apparatus of claim 18 further including address generating means for generating a series of successive address location signals during the course of said raster scan at said X-ray source, a second digital adder having first and second data inputs and having a data output connected to said one of said digital data storages, said first data input of said second digital adder being coupled to said address generating means, and a switch register of the form which stores and transmits a predetermined digital value, said switch register being connected to said second data input of said second digital adder.

21. The apparatus of claim 18 wherein said means for changing storage addresses enables selective displacing of addresses in either of said first and second digital data storages in either direction along two orthogonal coordinate axes.

22. The apparatus of claim 14 wherein said detectors include a plurality of detectors in addition to said first and second detectors each of which transmits an additional sequence of data values that is indicative of variations of X-ray intensity at a separate one of said detection points at successive times during the course of said raster scan, further including:
a plurality of data storages of the form which store successive data values at successive address locations,
means for transmitting each of said first, second and additional sequences of data values to a separate one of said data storages, and
wherein said means for combining data values shifts the addresses of data values in at least all but one of said data storages and then adds the data values stored at the same address in all of said data storages to produce said composite sequence of data values.

23. The apparatus of claim 14 further including means for storing a plurality of said composite sequences of data values each of which is descriptive of a separate one of a series of spaced parallel planar areas within said subject, and means for joining portions of successive ones of said plurality of composite sequences to produce an altered composite sequence that is descriptive of a differently oriented area.

24. The apparatus of claim 14 wherein said raster scan includes a plurality of parallel scan lines and wherein said means for combining individual data values produces successive data increments of said composite sequence by summing successive data values of at least said first and second sequences that originate from corresponding locations along two spaced apart ones of said raster scan lines.

25. The apparatus of claim 24 further including means for generating a plurality of said sequences of composite data values each of which is descriptive of a separate one of a series of parallel spaced apart planes within said subject, data storage means for storing the successive lines of data of each of said sequences of composite data values, and readout means for sequentially transmitting a line of data from each of said plurality of sequences to said display means to produce a tomographic image of an area that is angled relative to said parallel spaced apart planes.

26. The apparatus of claim 14 wherein said means for combining individual data values includes a digital computer having said particular locations and said predetermined different locations stored therein.

27. Apparatus for producing a tomographic image of a predetermined plane within a subject comprising:
an X-ray source having means for traveling an X-ray origin point through a raster scan which includes a plurality of sequential parallel scan lines, a plurality of X-ray detectors spaced apart from said source and being positioned to detect X-rays at detection points which are spaced apart in a direction parallel to the plane of said raster scan, each of said detectors having means for generating a signal during the course of each raster scan line in accordance with variations of the detected X-ray intensity at successive times during the course of the raster scan line, means for digitizing said detector signals to produce a plurality of primary sequences of data values, means for adding individual data values from each of said primary sequences that originate at predetermined different times during the course of said raster scan to produce a sequence of composite data values, a display device having means for displaying an image corresponding to at least a portion of said raster scan by traveling a light origin point along a plurality of sequential parallel scan lines, and means for modulating said light origin point during said travel thereof along said parallel scan lines in accordance with variations of the successive data values of said composite sequence of data values.

* * * * *

UNITED STATES PATENT AND TRADEMARK OFFICE
CERTIFICATE OF CORRECTION

PATENT NO. : 4,730,350
DATED      : March 8, 1988
INVENTOR(S) : Richard D. Albert It is certified that error appears in the above—identified patent and that said Letters Patent is hereby corrected as shown below:

Column 5,  line 37, "predetermiend" should be --predetermined--;
Column 5,  line 60, "processes" should be --processed--;
Column 5,  line 64, "signal" should be --signals--;
Column 8,  line 28, "values" should be --value--;
Column 8,  line 57, "timer" should be --time--;
Column 10, line 23, "in" should be --if--;
Column 11, line 9,  "travel" should be --travels--;
Column 19, line 67, "from" should be deleted;
Column 20, line 1,  "to" should be --at--;
Column 23, line 23, "a" should be --at--;
Column 23, line 43, "of" (second occurrence) should be deleted;
Column 24, line 67, after "locations", insert --that are offset from the particular locations--;
Column 25, line 67 (Claim 11, line 1), "digitized" should be --digitizing--
Column 25, line 68 (Claim 11, line 2), after "each" insert --successive--;
Column 27, line 17 (Claim 16, line 5), after "the" (second occurrence) insert --value--;
Column 27, line 52 (Claim 18, line 13) "sotrage" should be --storage--.

Signed and Sealed this

Twelfth Day of July, 1988

*Attest:*

DONALD J. QUIGG

*Attesting Officer*         *Commissioner of Patents and Trademarks*